United States Patent [19]

Chu et al.

[11] Patent Number: 5,179,104

[45] Date of Patent: Jan. 12, 1993

[54] PROCESS FOR THE PREPARATION OF ENANTIOMERICALLY PURE β-D-(−)-DIOXOLANE-NUCLEOSIDES

[75] Inventors: Chung K. Chu, Athens; Raymond F. Schinazi, Decatur, both of Ga.

[73] Assignee: University of Georgia Research Foundation, Inc., Athens, Ga.

[21] Appl. No.: 622,762

[22] Filed: Dec. 5, 1990

[51] Int. Cl.$^5$ .................. C07D 405/04; C07D 473/00
[52] U.S. Cl. .................................. 544/310; 544/180;
544/215; 544/264; 544/265; 544/276; 544/277;
544/309; 544/312; 549/214; 549/358; 549/397;
549/449; 549/453
[58] Field of Search ............. 544/310, 261, 262, 266,
544/277, 317, 180, 215, 264, 265, 276, 309, 312;
549/214, 358, 397, 449, 453

[56] References Cited

U.S. PATENT DOCUMENTS 5,041,449 8/1991 Belleau et al. ........................ 544/313

FOREIGN PATENT DOCUMENTS 0382526 8/1990 European Pat. Off. .

OTHER PUBLICATIONS

Bamford et al, J. Med. Chem. 1990, 33, 2494–2501.
Acton et al. J. Med. Chem. 1979, 22, 518–525.
Shuto et al, Chem. Pharm. Bull., vol. 36 (1988) p. 5020.
Mitsuya, H., et al., S. Proc. Natl. Acad. Sci. U.S.A., 83, 1911 (1986).
Chu, C. K., et al., J. Med. Chem., 32, 612 (1989).
Yarchoan, R., et al., Science, 245, 412 (1989).
Lin, T. S., et al., Biochem. Pharmacol., 36, 311 (1987).
Hamamoto, Y., et al., Antimicrob. Agents Chemother., 31 907 (1987).
Balzarini, J., et al., Biochem. Biophys. Res. Commun., 140, 735 (1987).
Martin, T. A., et al., J. Med. Chem., 33, 2137 (1990).
Furman, P. A., et al., Proc. Natl. Acad. Sci. U.S.A., 83, 8333 (1986).
Cheng, Y. C., et al., J. Biol. Chem., 262, 2187 (1987).
St. Clair, M. H., et al., Antimicrob. Agents Cemother., 31, 1972 (1987).
Schinazi, R. F., et al., Antimicrob. Agents Chemother., 33, 115 (1989).
Van Roey, P., et al., J. Am. Chem. Soc., 110, 2277 (1988).
Van Roey, P., et al., Proc. Natl. Acad. Sci. U.S.A., 86, 3929 (1989).
Norbeck, D. W., et al., Tet. Lett., 30, 6263 (1989).
Belleau, et al., Fifth Intl. Conf. on AIDS, Montreal, Canada, paper No. T.C.O.1. (Jun. 4–9, 1990).
Sterzycki, R. Z., et al., J. Med. Chem. 33, 2150 (1990).
Watanabe, K. A., et al., J. Med. Chem., 33, 2145 (1990).
Eriksson, B. F. H., et al., Antimicrobial Agents and Chemotherapy, 33, 10, 1729–1734.

Primary Examiner—Cecilia Shen
Attorney, Agent, or Firm—Kilpatrick & Cody

[57] ABSTRACT

An asymmetric process for the preparation of enantiomerically pure β-D-(−)-dioxolane-nucleosides. The enantiomerically pure dioxolane nucleosides are active HIV agents, that are significantly more effective than the prior prepared racemic mixtures of the nucleosides. The anti-viral activity of the compounds is surprising in light of the generally accepted theory that moieties in the endo conformation, including these dioxolanes, are not effective antiviral agents. The toxicity of the enantiomerically pure dioxolane nucleosides is lower that that of the racemic mixture of the nucleosides, because the nonnaturally occurring α-isomer is not included.

The product can be used as a research tool to study the inhibition of HIV in vitro or can be administered in a pharmaceutical composition to inhibit the growth of HIV in vivo.

14 Claims, 3 Drawing Sheets

PROCESS FOR THE PREPARATION OF ENANTIOMERICALLY PURE β-D-(−)-DIOXOLANE-NUCLEOSIDES

The government has rights in this invention by virtue of grants from the Public Health Service of the National Institute of Allergy and Infectious Diseases, and the Department of Veteran's Affairs that partially funded research leading to this invention.

BACKGROUND OF THE INVENTION

This invention is in the area of organic synthesis of nucleosides, and in particular relates to a process for the preparation of enantiomerically pure β-D-(−)-dioxolane nucleosides.

A number of 2',3'-dideoxynucleosides have been found to be potent antiviral agents against human immunodeficiency virus (HIV), the causative agent of acquired immunodeficiency syndrome (AIDS). The lead compound, AZT (Mitsuya, H.; Broder, S. *Proc. Natl. Acad. Sci. U.S.A.*, 1986 83, 1911) has been approved by the U.S. Food and Drug Administration for patients with AIDS and AIDS-related complex. Several other 2',3'-dideoxynucleosides are undergoing various stages of clinical trials, including 3'-azido-2',3'-dideoxyuridine (AZDU or CS-87, see, Chu, C. K.; et al., *J. Med. Chem.*, 1989, 32, 612; and Eriksson, B. F. H.; et al., *Antimicrob. Agents Chemother.*, 1989, 33, 1927), 2',3'-dideoxyinosine (DDI) and 2',3'-dideoxycytidine (DDC) (see Yarchoan, R. et. al., *Science,* 1989, 245, 412), 3'-deoxy-2',3'-didehydrothymidine (D4T, Lin, T. S., et al., *Biochem. Pharmacol.*, 1987, 36, 311; Hamamoto, Y., et al., *Antimicrob. Agents Chemother.*, 1987, 31, 907; Balzarini, J., et al., *Biochem. Biophys. Res. Commun.*, 1987, 140, 735), and 2'-fluoro-arabinofuranosyl- 2'-3'-dideoxycytidine (Martin, T. A., et al., *J. Med. Chem.*, 1990, 33, 2137; Watanabe, K. A., et al., *J. Med. Chem.*, 1990, 33, 2145; Sterzycki, R. Z., et al., *J. Med. Chem.*, 1990 33, 2150).

In the 5'-triphosphorylated form, these nucleosides are known to inhibit HIV reverse transcriptase as well as cause chain-termination of the growing viral DNA chain. Furman, P. A., et al., *Proc. Natl. Acad. Sci. U.S.A.,* 1986, 83, 8333; Cheng, Y. C., e al., *J. Biol. Chem.*, 1987, 262, 2187; St. Clair, M. H., et al., *Antimicrob. Agents Chemother.*, 1987, 31, 1972; and Schinazi, R. F., et al., *Antimicrob. Agents Chemother.*, 1989 33, 115.

The stereochemistry of nucleoside derivatives play an important role in their biological activity. The C1' position of the ribose in the nucleoside (the carbon bound to the nitrogen of the heterocyclic base) is a chiral center because the carbon is attached to four different moieties. Likewise, there is an optically active center at C4' of the nucleoside (the ring carbon bound to the hydroxymethyl group that is phosphorylated in nucleotides). In the naturally occurring nucleosides, both the base attached to the C1' and the hydroxymethyl group attached to the C4' atom are in the β-configuration (above the plane of the sugar). The corresponding non-naturally occurring α-isomers (in which the moieties are below the plane of the sugar) are rarely biologically active, and are typically toxic.

An analysis of the solid-state conformations of six active and two inactive anti-HIV nucleoside agents was recently performed to attempt to correlate the presence or absence of certain stereochemical features with high HIV activity. Van Roey, P., et al., *J. Am. Chem. Soc.,* 1988, 110, 2277; and Van Roey, P., et al., *Proc. Natl. Acad. Sci. U.S.A.,* 1989, 86, 3929. The x-ray structures indicated that active anti-HIV nucleosides assume the C3'-exo or similar carbohydrate conformations while inactive compounds prefer the C3'-endo conformation. (Endo and exo refer to the conformations in which the atoms are at the same or opposite side of the sugar ring in relation to the base). The C3'-exo and C3'-endo conformations place the C5' atom in axial and equitorial positions, respectively. The position of the C5' atom affects the location of the 5'-hydroxyl group in relation to the base. Since the 5'-hydroxyl group is the site of phosphorylation of the nucleoside, its location with respect to the rest of the nucleoside is important.

Figure 1:
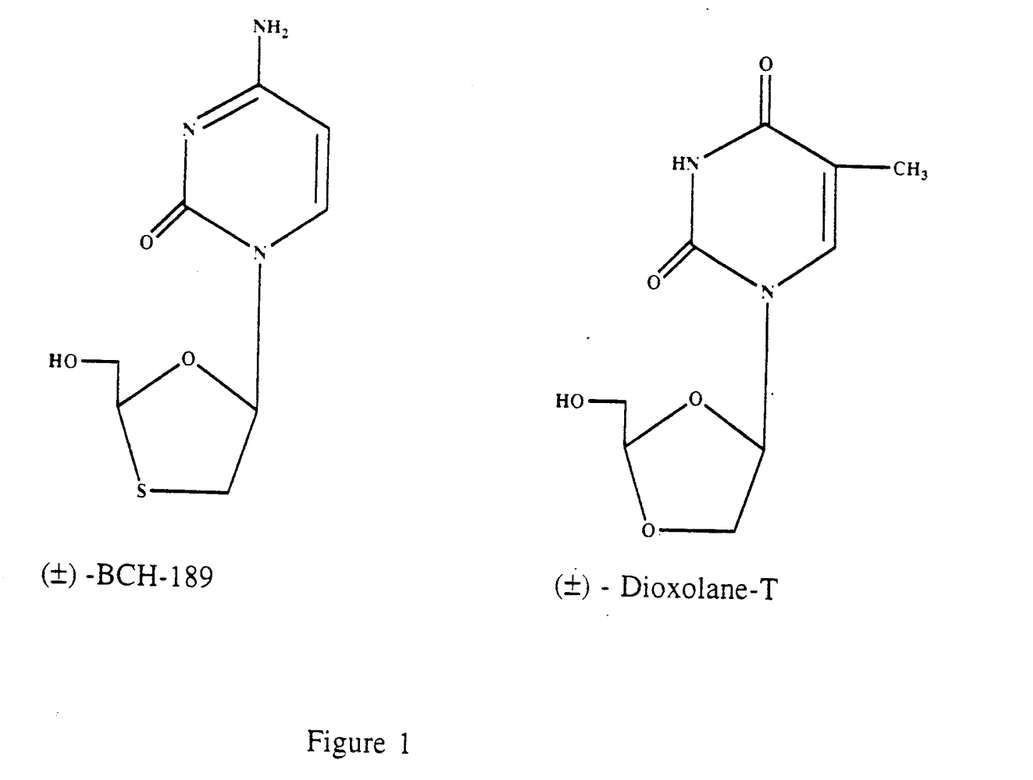
FIG. 1 is an illustration of the chemical structures of (±)-1-[(2β,4β)-2-(hydroxymethyl)-4-dioxolanyl]thymine (dioxolane-T) and (±)-1-[(2β,4β)-2-(hydroxymethyl)-4-(1,3-thioxolane)]thymine (BCH-189).

There has been recent interest in the synthesis of nucleoside derivatives in which the 3'-carbon of the nucleoside has been replaced with a heteroatom. Norbeck, D. W., et al., in *Tet. Lett.*, 1989, 30, 6263, reported the synthesis of (±)-1-[(2β,4β)-2-(hydroxymethyl)-4-dioxolanyl]thymine (referred to below as (±)-dioxolane-T, see FIG. 1), that results in a racemic mixture of diastereomers about the C4' atom. The product is a derivative of 3'-deoxythymidine in which the C3' atom has been replaced with an O3' atom. The product was synthesized in five steps from benzyloxyaldehyde dimethylacetal and (±)-methyl glycerate to produce a 79% yield of the 1:1 diastereomeric mixture. The X-ray crystallographic analysis of the product revealed that the dioxolane ring adopts the $^3T_4$ conformation commonly observed in ribonucleosides, with the O3' atom in the endo position. Norbeck reported that the racemic mixture of dioxolane-T exhibits an anti-HIV activity of 20 μM in ATH8 cells, and attributed the low efficacy against the virus to an effect of the endo conformation of the O3' atom.

Belleau, et al., in the Fifth International Conf. on AIDS, Montreal, Canada June 4–9, 1990, paper No. T.C.O.1, reported a method of synthesis of cytidine nucleosides that contain oxygen or sulfur in the 3' position. The dioxolane ring was prepared by the condensation of $RCO_2CH_2CHO$ with glycerine. As with the Norbeck synthesis, the Belleau synthesis results in a racemic mixture of diastereoisomers about the C4' carbon of the nucleoside. Belleau reported that the sulfur analog, referred to as NGBP-2I or (±) BCH-189 (see FIG. 1), had high anti-HIV activity. (±) BCH-189 is currently undergoing preclinical toxicology.

To date, no one has reported a method of synthesis of a nucleoside analog with an oxygen in the 3'-position that results in an enantiomerically pure dioxolane nucleoside that has the same stereochemistry as the nucleosides found in nature (the β stereoisomer). There is a need for such a synthesis as a research tool to provide more information on the effect of stereochemistry on the anti-viral activity of nucleoside derivatives, and to provide new anti-HIV agents.

It is therefore an object of the present invention to provide a method of synthesis of enantiomericaly pure dioxolane nucleosides.

It is another object of the present invention to provide enantiomerically pure dioxolane nucleosides with significant anti-HIV activity.

SUMMARY OF THE INVENTION

The invention as disclosed is an asymmetric process for the preparation of enantiomerically pure β-D-(−)-dioxolane-nucleosides. The process involves the initial preparation of (2R,4R)- and (2R,4S)-4-acetoxy-2-

(protected-oxymethyl)-dioxolane from 1,6-anhydromannose, a sugar that contains all of the necessary stereochemistry for the enantiomerically pure final product, including the correct diastereomeric configuration about the 1 position of the sugar (that becomes the 4'-position in the later formed nucleoside).

The (2R,4R)- and (2R,4S)-4-acetoxy-2-(protected-oxymethyl)dioxolane is condensed with a desired heterocyclic base in the presence of $SnCl_4$, other Lewis acid, or trimethylsilyl triflate in an organic solvent such as dichloroethane, acetonitrile, or methylene chloride, to provide the stereochemically pure dioxolanenucleoside.

The enantiomerically pure dioxolane nucleosides are active HIV agents, that are significantly more effective than the prior prepared racemic mixtures of the compounds. The anti-viral activity of the compounds is surprising in light of the generally accepted theory that moieties in the endo conformation, including these dioxolanes, are not effective antiviral agents. Further, the enantiomerically pure dioxolane nucleosides are less toxic than the racemic mixture of nucleosides because the nonnaturally occurring isomer has been eliminated.

The product can be used as a research tool to study the inhibition of HIV in vitro or can be administered in a pharmaceutical composition to inhibit the growth of HIV in vivo.

DETAILED DESCRIPTION OF THE INVENTION

I. Preparation of Enantiomerically Pure Dioxolane Nucleosides

In preparing enantiomerically pure dioxolane nucleosides, care should be taken to avoid strong acidic conditions that would cleave the dioxolane ring. Reactions should be performed, if possible, in basic or neutral conditions, and when acidic conditions are necessary, the time of reaction should be minimized.

A. Preparation of Dioxolane Derivative

Figure 2:
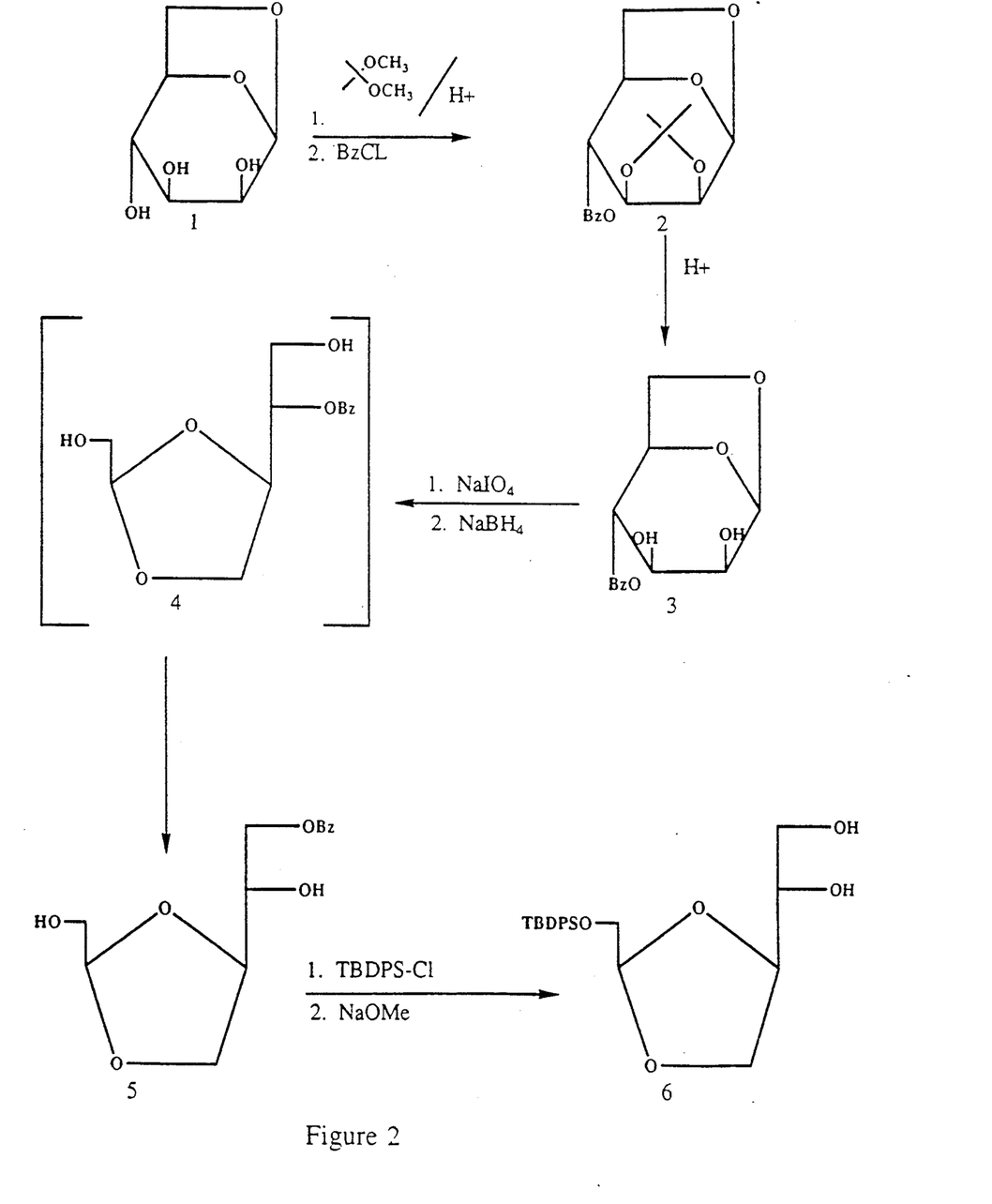
FIG. 2 is an illustration of the method of synthesis of enantiomerically pure β-D-(−)-dioxolane-thymine.

The key starting material for the synthesis of enantiomerically pure β-D-(−)-dioxolane-nucleosides is 1,6-anhydromannose (compound 1, FIG. 2). This sugar contains all of the necessary stereochemistry for the enantiomerically pure final product (see for example, compound 11, FIG. 2), including the correct diastereomeric configuration about the 1 position of the sugar (that becomes the 4'-position in the later formed nucleoside). 1,6-Anhydromannose can be prepared according to procedures described in Knauf, A. E.; Hann, R. M.; Hudson, C. S. *J. Am. Chem. Soc.*, 1941, 63, 1447; and Zottola, M. A.; Alonso, R.; Vite, G. D.; Fraser-Reid, B. *J. Org. Chem.*, 1989, 54, 6123. Prior syntheses of dioxolane nucleosides have used racemic mixtures of starting materials for the preparation of the ribose moiety. When the syntheses begin with a racemic mixture of reagents, undesirable racemic mixtures of enantiomeric nucleoside products have been produced. The mixtures are very difficult to separate and significantly increase the cost of the final product. Further, the inclusion of non-naturally occurring isomers increases the toxicity of the product.

The 1,6-anhydromannose is converted to its isopropylidene derivative with dimethoxypropane and p-toluenesulfonic acid, which, without isolation, is benzoylated in the 4-position to compound 2 (see FIG. 2). An acyl group can also be used to protect the 4-position. The isopropylidene group of compound 2 is then removed by a catalytic amount of an acid such as sulfuric acid, hydrochloric acid, formic acid, trifluoroacetic acid, sulfamic acid, in 60% aqueous dioxane or other suitable organic solvent at a temperature range of approximately 0° to 50° C. to give (−)-1,6-anhydro-4-0-benzoyl-β-D-mannopyranose in high yield as a white solid.

In the next step, the glycol of (−)-1,6-anhydro-4-0-benzoyl-β-D-mannopyranose is oxidatively cleaved by treatment with $NaIO_4$ in $H^2O$/EtOH (1:1) for one hour at approximately room temperature to produce to the corresponding dialdehyde. Lead tetraacetate can also be used as the oxidizing reagent for this reaction. The dialdehyde is immediately reduced in situ with any suitable reducing agent, including $NaBH_4$, diisobutylaluminum hydride (DIBAL-H), lithium borohydride ($LiBH_4$), or sodium bis(2-methoxyethoxy)aluminum hydride (Red-Al), at approximately room temperature or below. Under the conditions of reaction, compound 4 isomerizes by benzoyl migration from a secondary to a primary position to produce (−)-(2R,4R)-4-(2-benzoxy-1-hydroxyethyl)-2-(hydroxymethyl)dioxolane (compound 5, FIG. 2).

The 2-position of the dioxolane is then protected with a suitable oxygen protecting group, for example, a tri-substituted silyl group such as trimethylsilyl, dimethylhexylsilyl, t-butyldimethylsilyl, t-butyldiphenylsilyl, trityl, alkyl group, acyl groups such as acetyl, propionyl, benzoyl, p-$NO_2$ benzoyl, or toluyl, methylsulfonyl, or p-toluylsulfonyl. A preferred protecting group is t-butyldiphenylsilyl. After protecting the 2-position of the dioxolane, the benzoyl group is removed from the 2-hydroxyethyl-position with a strong base such as sodium methoxide or ammonia in methanol at approximately 0° to 50° C. to produce (−)-(2R,4R)-2-(protected-O-methyl)-4-(1,2-dihydroxyethyl)-dioxolane (compound 6, FIG. 2) in high yield.

In the next step, the 1,2-dihydroxyethyl group in the 4-position of the dioxolane is converted to a carboxylic acid with an oxidizing agent such as $NaIO_4/RuO_2$, or lead tetraacetate, at approximately 0° to 50° C. to produce (+)-(2R,4R)-2-(protected-oxymethyl)-4-carboxyldioxolane (see compound 7, FIG. 2).

A modified Hunsdiecker reaction (Dhavale, D.; et al., *Tetrahedron Lett.*, 1988, 29, 6163) is then carried out in ethyl acetate with Pb(OAc)$_4$, to convert (+)-(2R,4R)-2-(protected-oxymethyl)-4-carboxyldioxolane to the corresponding key intermediates (2R,4R)- and (2R,4S)-4-acetoxy-2-(protected-oxymethyl) dioxolane (see compound 8, FIG. 2) in good yield.

B. Condensation of a Heterocyclic Base with the Dioxolane Derivative

In the next step of this reaction scheme, the enantiomerically pure dioxolane prepared as described in Section A. is condensed with a protected base in the presence of trimethylsilyl triflate (trimethylsilyl trifluoromethanesulfonate) or a Lewis acid in a dry organic solvent.

Any compound containing a nitrogen that is capable of reaction with a center of electron deficiency can be used in the condensation reaction. Purine bases include adenine, hypoxanthine, $N^6$-alkylpurines, $N^6$-benzylpurine, $N^6$-halopurine, and guanine. Pyrimidine bases include thymine, cytosine, 6-azapyrimidine, 2-mercaptopyrimidine, and uracil. A thymine base is preferred in a condensation reaction carried out with a dioxolane derivative, and a cytosine base is preferred when the condensation reaction is carried out with a 1,3-thioxolane.

Functional oxygen and nitrogen groups on the heterocyclic base should be protected before condensation with the sugar. Protecting groups are well known to those skilled in the art, and include trimethylsilyl, dimethylhexylsilyl, t-butyldimethylsilyl, and t-butyldiphenylsilyl, tritylmethyl, alkyl groups, acyl groups such as acetyl and propionyl, methylsulfonyl, and p-toluylsulfonyl.

Friedel-Crafts catalysts (Lewis acids) that can be used in the condensation reaction include $SnCl_4$, $ZnCl_4$, $TiCl_4$, $AlCl_3$, $FeCl_3$, $BF_3$-diethylether, and $BCl_3$. These catalysts require anhydrous conditions because the presence of water reduces their activity. The catalysts are also inactivated in the presence of organic solvents with active hydrogens, such as alcohols and organic acids. The catalysts are typically used in solvents such as carbon disulfide, methylene chloride, nitromethane, 1,2-dichloroethane, nitrobenzene, tetrachloroethane, chlorobenzene, benzene, toluene, dimethylformamide, tetrahydrofuran, dioxane, or acetonitrile. Anhydrous aluminum chloride is not soluble in carbon disulfide. Niedballa, et al., *J. Org. Chem.* 39, 25 (1974). The preferred catalyst is $SnCl_4$. The preferred solvent is 1,2-dichloroethane.

Trimethylsilyl triflate can be used under the same conditions described above for the Friedel-Crafts catalysts. The reaction proceeds at a temperature range of from $-10°$ C. to $200°$ C.

The choice of catalyst for condensation will affect the final product ratio of to B nucleoside product. For example, condensation of the intermediates (2R,4R)- and (2R,4S)-4-acetoxy-2-(t-butyldiphenylsilyoxymethyl) dioxolane (compound 8, FIG. 2) with silylated thymidine in the presence of trimethylsilyl triflate in $CH_2Cl_2$ gave a mixture of (−)-1-[(2R,4R)-2-(t-butyldiphenylsilyloxymethyl)-4-dioxolanyl]thymine 9-β (45%) and (+)-1-[(2R,4S)-2-(t-butyldiphenylsilyloxymethyl)-4-dioxolanyl]thymine 10-α (29%). However, the reaction with $SnCl_4$ produced exclusively β-isomer 9 with trace amounts of α-isomer 10 detectable on TLC.

In the final step of this method of preparation of enantiomerically pure (−)-β-D-dioxolane-nucleosides, the 5′-O-position of the nucleoside is deprotected. Desilylation can be carried out with a variety of reagents, including acetic acid, trifluoroacetic acid, hydrogen fluoride, n-tetrabutylammonium fluoride, potassium fluoride and pyridinium HCl. For example, desilylation of compounds 9 and 10 with tetrabutylammonium fluoride gave the desired free nucleosides 11 and 12, respectively (FIG. 2). Acetic acid is preferred for commercial scale use because it is inexpensive. Other reagents for desilylation are known to those skilled in the art. Deacylation is accomplished in acid or base. 5-O-Ethers can be cleaved with $BCl_3$ or trimethylsilyl iodide.

The method of preparation of enantiomerically pure (−)-β-D-dioxolane-nucleosides is further illustrated in the following working example for the preparation of (−)-1-[(2B,4B)-2-(hydroxymethyl)-4-dioxolanyl]thymine, referred to as (−)-β-D-dioxolane-T. The enumeration of compounds in the working examples refer to structures set out in FIG. 2.

(−)-1,6-Anhydro-2,3-isopropylidene-4-O-benzoyl-β-D-mannopyranose 1,6-anhydro-β-D-mannopyranose (compound 1) was mixed with acetone (800 ml) and methanol (300 ml) and stirred for approximately thirty minutes until only a free-flowing solid remained. Dimethoxypropane (300 ml), and p-toluenesulfonic acid (5 g) were then added, and the mixture stirred for 2 hours.

The reaction mixture was then made basic with triethylamine (pH 8), and filtered to remove the white solid material. The solvents were evaporated, and the residue taken up in ethyl acetate and then crystallized to obtain 4 grams of the 2,3-isopropylidenated product as clear needles.

To a solution of the 1,6-anhydro-2,3-isopropylidene-β-D-mannopyranose (5.01 g, 0.025 mol) in pyridine (40 ml) was added dropwise benzoyl chloride (3.74 ml, 0.062 mol) at 0° C. The mixture was stirred for 45 minutes at 0° C. Ice was then added to the reaction mixture to remove excess of benzoyl chloride. The solvent was evaporated under vacuum and the residue was dissolved in ethyl acetate (200 ml). The organic layer was washed with water, sat. $NaHCO_3$ and brine. The resulting material was dried over anhydrous $MgSO_4$, filtered, and then evaporated to give (−)-1,6-anhydro-2,3-isopropylidene-4-O-benzoyl-β-D-mannopyranose crude product (compound 2, 8.7 g) as yellowish solid.

(−)-1,6-Anhydro-4-O-benzoyl-β-D-mannopyranose (3)

To a solution of 1,6-anhydro-4-O-benzoyl-2,3-isopropylidene-β-D-mannopyranose 2 (10.0 g, 32.6 mmole) in 60% aqueous dioxane (820 ml) was added concentrated $H_2SO_4$ (3.36 ml). The mixture was stirred at 70°–80° C. for 15 hours, and then cooled in an ice bath, neutralized with $NaHCO_3$ and concentrated until half of the original volume remained. The solution was then extracted with ethyl acetate and the combined organic layers washed with saturated NaHCO, solution and water, dried, and evaporated to give 3 as a white solid. The solid was crystallized from $CH_2Cl_2$-n-hexane to yield 3 (7.4 g, 85.3%) as white solid: $[\alpha]^{25}D -154.7°$ (C, 0.21 MwOH); $^1H$ NMR (DMSO-$d_6$): δ: 3.56–4.61 (m, 5H, 2,3,5,6-H), 4.82 (d, J=8.1 Hz, 1H, OH $D_2O$ exchangeable), 5.02 (s, 1H, 4-H), 5.09 (d, J=3.7 Hz, 1H, OH, $D_2O$ exchangeable), 5.28 (s, 1H, 1-H), 7.46–8.05 (m, 5H, Ar-H); IR (KBr) 3410, 1710 cm$^{-1}$; Anal. Calcd for $C_{13}H_{14}O_6$: C, 58.64; H, 5.31. Found: C, 58.51; H, 5.34.

(−)-(2R,4R)-4-(2-Benzoxy-1-hydroxyethyl)2-(hydroxymethyl)dioxolane (5)

To a solution of 3 (7.4 g, 27.8 mmole) in 95% ethanol (200 ml) was added a solution of $NaIO_4$ (6.54 g, 30.7 mmole) in water (200 ml). The mixture was stirred at room temperature for 1 hour. After checking to insure the complete conversion of diol to dialdehyde by thin layer chromatography, the reaction mixture was concentrated to the half of the original volume. Methanol (200 ml) was added to the residue and the mixture was cooled to 50° C. Sodium borohydride (4.2 g, 111.0 mmole) was added to the mixture portion-wise for 5 minutes and the mixture was stirred at 50° C. for 10 minutes, neutralized with glacial acetic acid and concentrated to yield crude 3 as yellow oil. The oil was purified by column chromatography over silica gel to yield pure 3 as colorless oil, that was crystallized from diethyl ether/n-hexane to yield 5 (6.12 g, 82%) as White solid: $[\alpha]^{25}D$ - 18.5° (C 0.20, methanol); $^1H$ NMR (DMSO-d$_6$): δ 3.47 (dd, J=5.9, 3.7 Hz, 2H, CH$_2$OH), 3.72–4.4 (m, 4H, 4, 5-H and CHOH), 4.27–4.95 (m, 2H, CH$_2$OB$_2$), 4.81–4.95 (m, 2-H and pri OH), 5.43 (d, J=5.5 Hz, 1H, sec OH, D$_2$O exchangeable), 7.43–8.09 (m, 5H, Ar-H); Anal. Calcd for C$_{13}$H$_{16}$O$_6$: C, 58.19; H, 6.02. Found: C, 58.09; H, 6.01.

(−)-(2R,4R)-4-(2-Benzoxy-1-hydroxyethy)-2-(t-bttuyldiphenylsilyloxy-methyl)-dioxolane To a solution of 3 (2.8 g, 10.4 mmole) and imidazole (2.04 g, 30.0 mmole) in dimethylformamide (40 ml) was added t-butyldiphenylsilyl chloride (3 ml, 11.5 mmole). The mixture was stirred at room temperature for 2 hours. The reaction mixture was evaporated to yield a yellow oil, that was purified by column chromatography over silica gel to yield (4.48 g, 85%) as a colorless oil; $[\alpha]^{25}D$ - 14.2° (C 0.26, methanol); $^1H$ NMR (DMSO-d$_6$): δ 1.00 (s, 9H, t-Bu), 3.68–3.87 (m, 3H, CH$_2$OTBDPS and CHOH), 3.98–4.16 (m, 3H, 4,5-H), 4.20–4.55 (m, 2H, CH$_2$OBz), 5.07 (t, J=3.3 Hz, 1H, 2-H), 5.47 (d, J-5.7 Hz, 1H, OH, D$_2$O exchangeable), 7.40–8.33 (m, 1OH, Ar-H); Anal. Calcd for C$_{29}$H$_{34}$O$_6$Si: C, 68.73; H, 6.79. Found: C, 68.86; H, 6.83.

(−)-(2R,4R)-2-(t-Butyldiphenylsilyloxymethyl)-4-(1,2-dihydroxyethyl)-dioxolane (6)

To a solution of (−)-(2R,4R)-4-(2-benzoxy-1-hydroxyethyl)-2-(t-butyldiphenylsilyloxy-methyl)-dioxolane (2.52 g, 5.0 mmole) in methanol (40 ml) was added a 0.078 M solution of sodium methoxide (7.3 ml) in methanol. The mixture stirred at room temperature for two hours. The mixture was neutralized with acetic acid and concentrated. The residue was then portioned between ethyl acetate and water, and the aqueous layer extracted with ethyl acetate. The combined organic layers were washed with a saturated NaHCO$_3$ solution and then water, and then dried, evaporated, and purified by column chromatography over silica gel to yield 6 (1.9 g, 95%) as colorless oil: $[\alpha]^{25}$D-2° (C 0.25, MeOH); $^1H$ NMR (DMSO-d$_6$) δ 1.00 (s, 9H, t-Bu), 3.40–3.52 (m, 3H, CH$_2$OH and CHOH), 3.64 (d, J=3.7 Hx, 2H, CH$_2$OTBDPS), 3.82–3.95 (m, 3H, 4,5-H), 4.49 (t, J-5.3 Hz, 1H, pri OH, D$_2$O exchangeable), 4.82 (d, J=5.1 Hz, 1H, sec OH, D$_2$O exchangeable), 5.01 (t, J-3.7 Hz, 1H, 2-H), 7.36–7.71 (m, 10H, Ar-H); Anal. Calcd for C$_{22}$H$_{33}$H$_{30}$O$_5$Si: C, 65.63; H, 7.53. Found: C, 65.72; H, 7.52.

(+)-(2R,4R)-2-(t-Butyldiphenylsilyloxymethyl)-4-carboxyldioxolane (7)

To a biphasic solution of 6 (1.6 g, 4.0 mmole) in CH$_3$CN (8 ml), CCl$_4$ (8 ml) and H$_2$O (12 ml) was added NaIO$_4$ (3.59 g, 16.8 mmole) and RuO$_2$ hydrate (8.5 mg). The mixture was vigorously stirred at room temperature for 5 hours. Methylene chloride (40 ml) was added to the mixture. The organic layer was separated. The aqueous layer was extracted with CH$_2$Cl$_2$. The combined organic layers were washed with water, filtered through celite pad and then concentrated to yield crude 7 (1.2 g, 77.4%) as black oil, that was used in the next reaction without further purification. For analytical purposes crude 7 was purified by column chromatography over silica gel to yield 7 as a white foam: $[\alpha]^{25}D+15.7°$ (C 0.28, MeOH); $^1H$ NMR (DMSO-d$_6$) δ 0.99 (s, 9H, t-Bu), 3.43–4.05 (m, 4H, 5-H and CH$_2$OTBDPS), 4.25 (t, J=6.8 Hz, 1H, 4-H), 5.04 (dd, J=5.1, 3.7 Hz, 1H, 2-H), 7.38–7.72 (m, 10H, Ar-H).

(2R,4R)- and (2R,4S)-4-Acetoxy-2-(t-butyldiphenylsilyoxymethyl) dioxolane (8)

To a solution of 7 (0.46 g, 1.14 mmole) in ethyl acetate (10 ml) was added pyridine (0.09 ml, 1.25 mmole) and Pb(OAc)$_4$ (0.66 g, 1.49 mmole). The mixture was stirred at room temperature for 15 hours under N$_2$, and then filtered through celite pad, and then concentrated and purified by column chromatography over silica gel to yield 8 (0.29 g, 63.5%) as a colorless oil: $^1H$ NMR (CDCl$_3$) δ 1.06 and 1.10 (s, 9H, t-Bu), 1.92 and 2.06 (s, 1H, CH$_3$), 3.71–4.24 (m, 4H, 5-H and CH$_2$OTBDPS), 5.25 and 5.38 (t, J=4.3 and 3.3 Hz each, 1H, 2-H), 6.27–6.41 (m, 1H, 4-H), 7.20–7.72 (m, 10H, Ar-H); IR (KBr) 3400, 1620 cm$^{-1}$.

(−)-1-[(2R,4R)-2-(t-Butyldiphenylsilyloxymethyl)-4-dioxolanyl]thymine (9) and
(+)-1-[(2R,4s)-2-(t-Butyldiphenylsilyloxymethyl)-4-dioxolanyl] thymine (10)

To a suspension of thymine (0.15 g, 1.2 mmole) in haxamethyldisilazane (10 ml) was added a catalytic amount of (NH$_4$)$_2$SO$_4$, and the mixture refluxed for 3 hours. The clear solution obtained was concentrated to yield silylated thymine as a colorless oil. A solution of 8 (0.24 g, 0.6 mmole) in CH$_2$Cl$_2$ (5 ml) was added to a solution of silylated thymine in CH$_2$Cl$_2$ (5 ml) and the mixture cooled to 5° C. To the cooled mixture was added trimethylsilyl triflate (0.23 ml, 1.2 mmole), and the mixture stirred at room temperature for 1 hour under N$_2$. A saturated NaHCO$_3$ solution (20 ml) was added to the mixture, and the mixture again stirred at room temperature for 30 minutes. The organic layer was then separated and the aqueous layer extracted with CH$_2$Cl$_2$. The combined organic layer was washed with a saturated NaHCO$_3$ solution and water, dried, concentrated and separated by column chromatography over silical gel to yield 9 (0.125 g, 44.6%) as white foam and 10 (0.08 g, 28.6%) as white foam: 9 (β-form); $[\alpha]^{25}D$ - 6.98° (C 0.43, MeOH); $^1H$ NMR (CDCl$_3$) δ 1.08 (s, 9H, t-Bu), 1.67 (s, 3H, CH$_2$), 3.92 (d, J=3.2 Hz, 2H, CH$_2$OTBDPS), 4.14 (d, J=4.0 Hz, 2H, 5-H), 5.06 (t, J=3.2 Hz, 1H, 2-H), 6.36 (t, J+4.0 Hz, 1H, 4-H), 7.26–7.75 (m, 10H, Ar-H), 9.51 (bnr s, 1H, H=NH): UV (MeOH) $\lambda_{max}$ 265.0 (pH 2); 264.4 nm (pH 11) Anal. Calcd for C$_{25}$H$_{30}$O$_5$N$_2$Si: C, 64.34; H, 6.49; N, 6.00. Found C, 64.28; H, 6.51; N, 5.98.

10 (α-form); $[\alpha]^{25}D+11.3°$ (C 0.23, MeOH); $^1H$ NMR (CDCl$_3$) δ 1.08 (s, 9H, t-Bu), 1.94 (d, J=1.2 Hz, 3H, CH$_3$), 3.70 (d, J=3.2 Hz, 2H, CH$_2$OTBDPS), 4.01 (dd, J=9.5, 2.3 Hz, 1H, 5H), 4.35 (dd, J=9.5, 5.3 Hz, 1H, 5-H), 5.55 (t, J=3.2 Hz, 1H, 2-H), 6.32 (dd, J=5.3, 2.3 Hz, 1H, 4-H), 7.17 (d, J=1.2 Hz, 1H, 6′-H), 7.37–7.74 (m, 10H, Ar-H), 9.57 (br s, 1H, NH); UV (MeOH) $\lambda_{max}$ 265.0; (pH 2); 264.5 nm (pH 11); Anal. Calcd for C$_{25}$H$_{30}$O$_5$N$_2$Si: C, 64.34; H, 6.49; N, 6.00. Found C, 64.23; H, 6.51; N, 5.93.

(−)-1-[(2R,4R)-2-(Hydroxymethyl)-4-dioxolanyl]thymine (11)

To a solution of (93.3 mg, 0.2 mmole) in tetrahydrofuran (THF) (3 ml) was added 1.0 M solution of tetra-n- butylammonium fluoride in THF (0.24 ml, 0.24 mmole) and the mixture stirred at room temperature for 1 hour. The mixture was then concentrated and purified by column chromatography over silica gel to yield 11 (42 mg, 92.1%) as white solid: $[\alpha]^{25}D -18.8°$ (C o.17, MeOH); $^1$H NMR (DMSO-$d_6$) δ 1.75 (d, J=1.2 Hz, 3H, CH$_3$) 3.63 (dd, J+6.0, 2.6 Hz, 2H, CH$_2$OH), 4.03 (dd, J=9.9, 5.5 Hz, 1H, 5-H), 4.22 (dd, J=9.9, 2.0 Hz, 1H, 5-H), 4.90 (t, J=2.6 Hz, 1H, 2-H), 5.16 (t, J-t.0 Hz, 1H, OH), 6.21 (dd, J=5.5, 2.0 Hz, 1H, 4-H), 7.67 (d, J=1.2 Hz, 1H, 6'-H), 11.27 (br s, 1H NH); UV (H$_2$) $\lambda_{max}$ 26o.0 (ε 10757); 266.5 (ε 9894) (pH 2); 266.3 (ε 8397) (pH 11); Anal. Calcd for C$_9$H$_{12}$O$_5$N$_2$: C, 47.36; H, 5.31; N, 12.28. found: c, 47.28; H, 5.34; N, 12.29.

(+)-1-[(2R,4S)-2-(hydroxymethyl)-4-dioxolanyl]thymine (12)

Deprotection of 10 (60 mg, 0.13 mmole) according to same procedure as described above for 11 yielded 12 (26 mg, 87.6%) as a white foam: $[\alpha]^{25}D +10.7°$ (C 0.15, MeOH); $^1$H NMR (DMSO-$d_6$) δ 1.79 (s, 3H, CH$_3$), 3.43 (dd, J=6.0, 3.7 Hz, 2H, CH$_2$OH), 4.02 (dd, J=9.5, 3.3 Hz, $^1$H, 5-H), 4.28 (dd, J=9.5, 5.6 Hz, 1H, 5-H), 5.00 (t, J=6.0 Hz, 1H, OH), 5.47 (t, J=3.7 Hz, 1H, 2-H), 6.17 (dd, J=5.6, 3.3 Hz, 1H, 4-H), 7.43 (d, J=1.2 Hz, 1H, 6'-H), 11.32 (br s, 1H NH); UV (H$_2$O) $\epsilon_{max}$ 266.5 (ε 9454); 266.5 (ε 9199) (pH 2); 266.3 (ε 6925) (pH=11); Anal. Calcd for C$_9$H$_{12}$O$_5$N$_2$: C, 47.36; H, 5.31; N, 12.28. found: C, 47.22; H.5.32; N, 12.16.

II. Anti-HIV Activity of Dioxolane Nucleosides

In contrast to the previous report that β-D-(±)-dioxolane-thymine has low efficacy against HIV in ATH8 cells, the enantiomerically pure β form 11 exhibited a potent anti-HIV activity (EC$_{50}$=0.3 μM). It was surprising to discover that enantiomerically pure β-D-(−)-dioxolane-T has significantly higher anti-HIV activity than the racemic mixture of the compound. This difference might be explained based on the rate of phosphorylation of 11 in these systems. As expected, the α-isomer 12 did not exhibit any significant anti-HIV activity.

β-D-(−)-Dioxolane-nucleosides can be used as research tools to inhibit the growth of HIV in vitro, or can be administered pharmaceutically to inhibit the growth of HIV in vivo.

The ability of β-D-(−)-dioxolane-nucleosides to inhibit HIV can be measured by various experimental techniques. The technique used herein, and described in detail below, measures the inhibition of viral replication in phytohemagglutinin (PHA) stimulated human peripheral blood mononuclear (PBM) cells infected with HIV-1 (strain LAV). The amount of virus produced is determined by measuring the virus-coded reverse transcriptase enzyme. The amount of enzyme produced is compared to an HIV control. The method is described in detail below.

Antiviral and Cytotoxic Assay in Human Peripheral Blood Mononuclear Cells

A. Three-day-old phytohemagglutinin-stimulated PBM cells (10$^6$ cells/ml) from hepatitis B and HIV-1 seronegative healthy donors were infected with HIV-1 (strain LAV) at a concentration of about 100 times the 50% tissue culture infectious dose (TICD 50) per ml and cultured in the presence and absence of various concentrations of antiviral compounds.

B. Approximately 45 minutes after infection, the medium, with the compound to be tested (2 times the final concentration in medium) or without compound, was added to the flasks (5 ml; final volume 10 ml). AZT was used as a positive control.

C. The cells were exposed to the virus (about 2×10$^5$ dpm/ml, as determined by reverse transcriptase assay) and then placed in a CO$_2$ incubator. HIV-1 (strain LAV) was obtained from the Center for Disease Control, Atlanta, Ga. The methods used for culturing the PBM cells, harvesting the virus and determining the reverse transcriptase activity were those described by McDougal et al. (*J. Immun. Meth.* 76, 171-183, 1985) and Spira et al. (*J. Clin. Meth.* 25, 97-99, 1987), except that fungizone was not included in the medium (see Schinazi, et al., *Antimicrob. Agents Chemother.* 32, 1784-1787 (1988)). The reverse transcriptase activity in the virus-infected control was about 2×10$^5$ dpm per ml. Blank and uninfected cell control values were about 300 and 1,000 dpm, respectively. Similar results are obtained when Step C is performed before step B.

D. On day 6, the cells and supernatant were transferred to a 15 ml tube and centrifuged at about 900 g for 10 minutes. Five ml of supernatant were removed and the virus was concentrated by centrifugation at 40,000 rpm for 30 minutes (Beckman 70.1 Ti rotor). The solubilized virus pellet was processed for determination of the levels of reverse transcriptase. Results are expressed in dpm/ml of sampled supernatant.

The median effective (EC$_{50}$) concentration for (−)-1-[(2β,4β)-2-(hydroxymethyl)-4-dioxolanyl]thymine was determined by the median effect method (*Antimicrob. Agents Chemother.* 30, 491-498 (1986). Briefly, the percent inhibition of virus, as determined from measurements of reverse transcriptase, is plotted versus the micromolar concentration of compound. The EC$_{50}$ is the concentration of compound at which there is a 50% inhibition of viral growth.

The EC$_{50}$ of (−)-1-[(2β,4β)-2-(hydroxymethyl)-4-dioxolanyl]thymine in PBM cells was measured as 0.2 μM. This activity compares favorably with 2',3'-dideoxyadenosine (DDA, EC$_{50}$=0.91 μM), 3'-azido-2',3'-dideoxyuridine (AZDU, EC$_{50}$=0.18-0.46 μM), and 3'-dideoxythymidine (DDT, EC$_{50}$=0.17 μM), which are structurally similar compounds that are undergoing clinical phase testing in the FDA.

III. Toxicity of Dioxolane Nucleosides

Mitogen-stimulated uninfected human PBM cells (3.8×10$^5$ cells/ml) were cultured in the presence and absence of drug under similar conditions as those used for the antiviral assay described above. The cells were counted after 6 days using a hemacytometer and the trypan blue exclusion method, as described by Schinazi et al., *Antimicrobial Agents and Chemotherapy*, 22(3), 499 (1982). The IC$_{50}$ is the concentration of compound which inhibits 50% of normal cell growth.

The IC$_{50}$ of (−)-1-[(2β,4β)-2-(hydroxymethyl)-4-dioxolanyl]thymine was measured as over 100 μM, indicating that the compound was not toxic in uninfected PBM cells evaluated up to 100 μM.

IV. Preparation of Pharmaceutical Compositions

Humans suffering from diseases caused by HIV infection can be treated by administering to the patient an effective amount of β-D-(−)-dioxolane-nucleosides or their salts in the presence of a pharmaceutically acceptable carrier or diluent. The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to deliver to a patient a therapeutically effective amount of compound to inhibit HIV replication in vivo without causing serious toxic effects in the patient treated. By "HIV inhibitory amount" is meant an amount of active ingredient sufficient to exert an HIV inhibitory effect as measured by, for example, an assay such as the ones described herein.

These preparations should produce a serum concentration of active ingredient of from about 0.2 to 40 $\mu$M. A preferred concentration range is from 0.2 to 20 $\mu$M and most preferably about 1 to 10 $\mu$M.

The pharmaceutical compositions should provide a dosage of from 1 to 60 milligrams of compound per kilogram of body weight per day. The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

$\beta$-D-(−)-Dioxolane-nucleosides or their salts can be administered as a component of an elixir, suspension, syrup, wafer, chewing gum or the like. A syrup may contain, in addition to the active compounds, sucrose as a sweetening agent and certain preservatives, dyes and colorings and flavors.

$\beta$-D-(−)-Dioxolane-nucleosides or their salts can also be mixed with other active materials that do not impair the desired action, or with materials that supplement the desired action, such as antibiotics, antifungals, antiinflammatories, or other antivirals, including other nucleoside anti-HIV compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

V. Preparation of Phosphate Derivatives of $\beta$-D-(−)-Dioxolane-Nucleosides Mono, di, and triphosphate derivative of $\beta$-D-(−)-dioxolane-nucleosides can be prepared as described below.

The monophosphate can be prepared according to the procedure of Imai et al., *J. Org. Chem.*, 34(6), 1547–1550 (June 1969). For example, about 100 mg of $\beta$-D-(−)-dioxolane-nucleoside and about 280 $\mu$l of phosphoryl chloride are reacted with stirring in about 8 ml of dry ethyl acetate at about 0° C. for about four hours. The reaction is quenched with ice. The aqueous phase is purified on an activated charcoal column, eluting with 5% ammonium hydroxide in a 1:1 mixture of ethanol and water. Evaporation of the eluant gives ammonium-(β-D-(−)-dioxolane-nucleoside)-5'-monophosphate.

The diphosphate can be prepared according to the procedure of Davisson et al., *J. Org. Chem.*, 52(9), 1794–1801 (1987). β-D-(−)-Dioxolane-nucleosides can be prepared from the corresponding tosylate, that can be prepared, for example, by reacting the nucleoside with tosyl chloride in pyridine at room temperature for about 24 hours, working up the product in the usual manner (e.g., by washing, drying, and crystallizing it).

The triphosphate can be prepared according to the procedure of Hoard et al., *J. Am. Chem. Soc.*, 87(8), 1785–1788 (1965). For example, β-D-(−)-dioxolane-nucleoside is activated (by making a imidazolide, according to methods known to those skilled in the art) and treating with tributyl ammonium pyrophosphate in DMF. The reaction gives primarily the triphosphate of the nucleoside, with some unreacted monophosphate and some diphosphate. Purification by anion exchange chromatography of a DEAE column is followed by isolation of the triphosphate, e.g., as the tetrasodium salt.

This invention has been described with reference to its preferred embodiments. Variations and modifications of the invention, enantiomerically pure β-D-(−)-dioxolane-nucleosides, will be obvious to those skilled in the art from the foregoing detailed description of the invention. It is intended that all of these variations and modifications be included within the scope of the appended claims.

We claim:

1. A process for the preparation of enantiomerically pure β-D-(−)-dioxolane-nucleosides comprising preparing the dioxolane ring from 1,6-anhydromannose.

2. The process of claim 1 further comprising converting 1,6-anhydromannose to its (2,3)-isopropylidene derivative.

3. The process of claim 2 further comprising benzoylating the 2,3-isopropylidene derivative of 1,6-anhydromannose to (−)-1,6-anhydro-4-O-benzoyl-2,3-isopropylidene-β-D-mannopyranose.

4. The process of claim 3, further comprising oxidizing the (−)-1,6-anhydro-4-O-benzoyl-2,3-isopropylidene-β-D-mannopyranose to (−)-(2R,4R)-4-(2-benzoxy-1-hydroxyethyl)-2-(hydroxymethyl)dioxolane.

5. The process of claim 4, further comprising protecting the 2-hydroxy position of the dioxolane with an oxygen protecting group.

6. The process of claim 5, wherein the oxygen protecting group is selected from the group consisting of trimethylsilyl, dimethylhexylsilyl, t-butyldimethylsilyl, t-butyldiphenylsilyl, trityl, alkyl groups, acetyl, propionyl, benzoyl, p-$NO_2$ benzoyl, toluyl, methylsulfonyl, and p-toluylsulfonyl.

7. The process of claim 5, further comprising removing the benzoyl group from the 2-hydroxyethyl-position to produce (−)-(2R,4R)-2-(protected-O-methyl)-4-(1,2-dihydroxyethyl)-dioxolane.

8. The process of claim 7, further comprising oxidizing the (+)-(2R,4R)-2-(protected-oxymethyl)-4-carboxyldioxolane to form a compound selected from the group consisting of (2R,4R)- and (2R,4S)-4-acetoxy-2-(protected-oxymethyl)dioxolane.

9. The process of claim 8, further comprising converting (2R,4R)- and (2R,4S)-4-acetoxy-2-(protected-oxymethyl)-dioxolane to a product selected from the group consisting of (2R,4R)- and (2R,4S)-4-acetoxy-2-(protected-oxymethyl)-dioxolane.

10. The process of claim 1, further comprising condensing the dioxolane ring with a purine or pyrimidine base.

11. The process of claim 8, further comprising condensing (2R,4R)- or (2R,4S)-4-acetoxy-2-(protected-oxymethyl)dioxolane with a purine or pyrimidine base.

12. The process of claim 10, wherein the purine or pyrimidine base is selected from the group consisting of adenine, hypoxanthine, $N^6$-alkylpurines, $N^6$-benzylpurine, $N^6$-halopurine, guanine, thymine, cytosine, 6-azapyrimidine, 2-mercaptopyrimidine, and uracil.

13. The process of claim 11, wherein the purine or pyrimidine base is selected from the group consisting of adenine, hypoxanthine, $N^6$-alkylpurines, $N^6$-halopurine, guanine, thymine, cytosine, 6-azapyrimidine, 2-mercaptopyrimidine, and uracil.

14. The process of claim 1, wherein the dioxolane nucleoside is (−)-1-[(2β,4β)-2-(hydroxymethyl)-4-dioxolanyl]thymine.

* * * * *